United States Patent [19]
von Bahr

[11] Patent Number: 6,080,583
[45] Date of Patent: Jun. 27, 2000

[54] BLOOD ANALYSIS SYSTEM AND METHOD FOR REGULATING SAME

[75] Inventor: Pontus von Bahr, Stockholm, Sweden

[73] Assignee: Siemens-Elema AB, Solna, Sweden

[21] Appl. No.: 09/082,442

[22] Filed: May 21, 1998

[30] Foreign Application Priority Data

Jun. 4, 1997 [SE] Sweden .................................. 9702118

[51] Int. Cl.[7] .................................................. G01N 31/00
[52] U.S. Cl. .............................................. 436/16; 422/68.1
[58] Field of Search ................................ 422/68.1, 82.05, 422/82.08, 82.09; 436/11, 16, 48, 164, 165

[56] References Cited

U.S. PATENT DOCUMENTS 3,874,850  4/1975  Sorensen et al. ...................... 23/230 B
4,399,362  8/1983  Cormier et al. ......................... 250/430
5,697,366  12/1997  Kimball et al. .......................... 128/632

OTHER PUBLICATIONS

"Integrated pO$_2$, pCO$_2$, pH Sensor System for Online Blood Monitoring," Gumbrecht et al., Sensors and Actuators, B 18–19 (1994) pp. 704–708.

*Primary Examiner*—Jill Warden
*Assistant Examiner*—Alex Noguerola
*Attorney, Agent, or Firm*—Hill & Simpson

[57] ABSTRACT

In a blood analysis system and method, a measurement unit with a measurement cell is alternately filled with blood and at least two specific fluids. At least one of the specific fluids serves as a calibration fluid for the measurement unit. A tag substance is added to at least one of the specific fluids to make the fluids distinguishable from each other and from blood, and the measurement unit includes a detector, arranged in the measurement cell, for determining the identity of fluid present in the measurement cell. The entire blood analysis system can be controlled and monitored on the basis of the identity of the fluid in the measurement cell.

14 Claims, 4 Drawing Sheets

BLOOD ANALYSIS SYSTEM AND METHOD FOR REGULATING SAME

BACKGROUND OF THE INVENTION

1. Field of the Invention

The present invention relates to a blood analysis system and to a method for regulating a blood analysis system.

2. Description of the Prior Art

A large amount of important information about a patient can be obtained from blood. A blood analysis can supply information about blood gases (e.g. $PO_2$ and $pCO_2$), pH value, metabolites (e.g. glucose and lactate), ions ($K^+$, $Na^+$, $Ca^{++}$ and $Cl^-$), hormones, antibodies, DNA, etc. One known blood analysis system is described in the article "Integrated $PO_2$, $pCO_2$, pH sensor system for online blood monitoring", Gumbrecht et al., Sensors and Actuators B, 18–19 (1994), pp 704–708. The known blood analysis system includes a tubing system which is connected to a patient's blood system and to two containers for different calibration fluids and to a collection vessel for spent fluids and blood. Pumps are arranged at the containers to pump fluids through the tubing system, and a measurement device is arranged in the tubing system to analyze blood samples. When a blood sample is to be analyzed, the pump at the collection vessel pumps blood from the patient toward the collection vessel until the measurement unit has filled with blood. The blood's oxygen, carbon dioxide and pH value are then determined by dedicated measurement sensors in the measurement unit. The calibration fluids are employed for two-point calibration of the measurement sensors in the measurement unit while simultaneously flushing all residual blood, which could otherwise affect subsequent measurements, out of the measurement unit.

The known system consumes a small amount of blood, i.e. about 15 μl, in each measurement. In other known systems, blood is pumped back to the patient's blood circulatory system.

Regardless of whether blood is consumed or pumped back to the patient, all the known blood analysis systems of this type have certain shortcomings. The blood analysis system must operate for years. The properties of pumps and tubing can change during usage or fail in some way. For example, pumps, usually peristaltic pumps, could affect the geometry of tubing so that the pump's capacity changes. Tubes could start leaking or become occluded, thereby affecting the flow of fluids in the tubes. As a rule, larger than necessary volumes are pumped to ensure that the correct amount of fluid (blood or calibration fluid) really is present in the measurement unit, thereby increasing the consumption of fluids. The only monitoring normally available is to recognize the unreasonable results which arise in the analyses of blood samples when major faults occur. Correcting a fault at this stage makes greater demands on both staff and equipment than if an alarm had been triggered before the fault became excessive. A number of erroneous measurements might have been made before the fault became big enough to affect measurements to any significant extent.

SUMMARY OF THE INVENTION

An object of the present invention is to provide a blood analysis system of the above type which simply and reliably ensures that measurement is performed on the right fluid.

Another object of the invention is to provide a blood analysis system according of the above type which makes possible simple, reliable and effective control of the blood analysis system, so consumption of fluids is minimized.

Another object of the invention is to provide a blood analysis system according of the above type which makes possible, simple, reliable and effective monitoring of the blood analysis system, so faults can be corrected without delay.

Yet another object of the invention is to provide a method for controlling a blood analysis system which simply and reliably eliminates the aforementioned problems.

The above object is achieved in a blood analysis system constructed and operating in accordance with the principles of the present invention wherein a measurement unit contains a measurement cell which is alternatingly filled with blood and one of at least two specific fluids, the at least two specific fluids including a calibration fluid for the measurement unit, and wherein at least one of the specific fluids has a distinguishable substance added thereto, and wherein the measurement unit includes a detector arranged in the measurement cell which determines the identity of the fluid in the measurement cell by means of the distinguishable substance which has been added thereto.

Identification of the fluid (or mixture of fluids) in the measurement cell affords a number of opportunities for controlling and monitoring the blood analysis system in a more reliable and effective fashion than is the case for known blood analysis systems. Distinguishability is achieved by the addition of appropriate substance to at least one of the fluids, so calibration fluids, flushing solutions and blood can easily be individually identified by a detector in the measurement cell.

The distinguishable substance can have differing color, differing optical characteristics, differing acoustical properties or differing electric/magnetic properties. Identification can then be performed optically (e.g. by absorption or color analysis), acoustically (e.g. ultrasonically) or electrically/magnetically (e.g. by measurement of capacitance or electromotive force)

When necessary, further fluids could be tagged with another substance, having differing properties relative to the first substance.

The initially-cited objects are also achieved in a method for regulating a blood analysis system wherein a first fluid is pumped into a measurement cell, the identity of fluid which is present in the measurement cell is determined by monitoring the presence of a distinguishable substance in the first fluid, the pumping is terminated when the measurement cell is filled with the first fluid, at least one measurement sensor in the measurement cell is then calibrated for the first fluid, a blood sample is pumped into the measurement cell and the presence of blood in the measurement cell is determined, pumping is terminated when the measurement cell has filled with blood, and at least one parameter in the blood is measured using the measurement sensor.

When the pumps are controlled according to identification of the fluid in the measurement cell, control with minimal consumption of fluids is achieved while still ensuring that only one fluid (blood or a calibration solution) is measured at a time.

DESCRIPTION OF THE PREFERRED EMBODIMENTS

Figure 1:
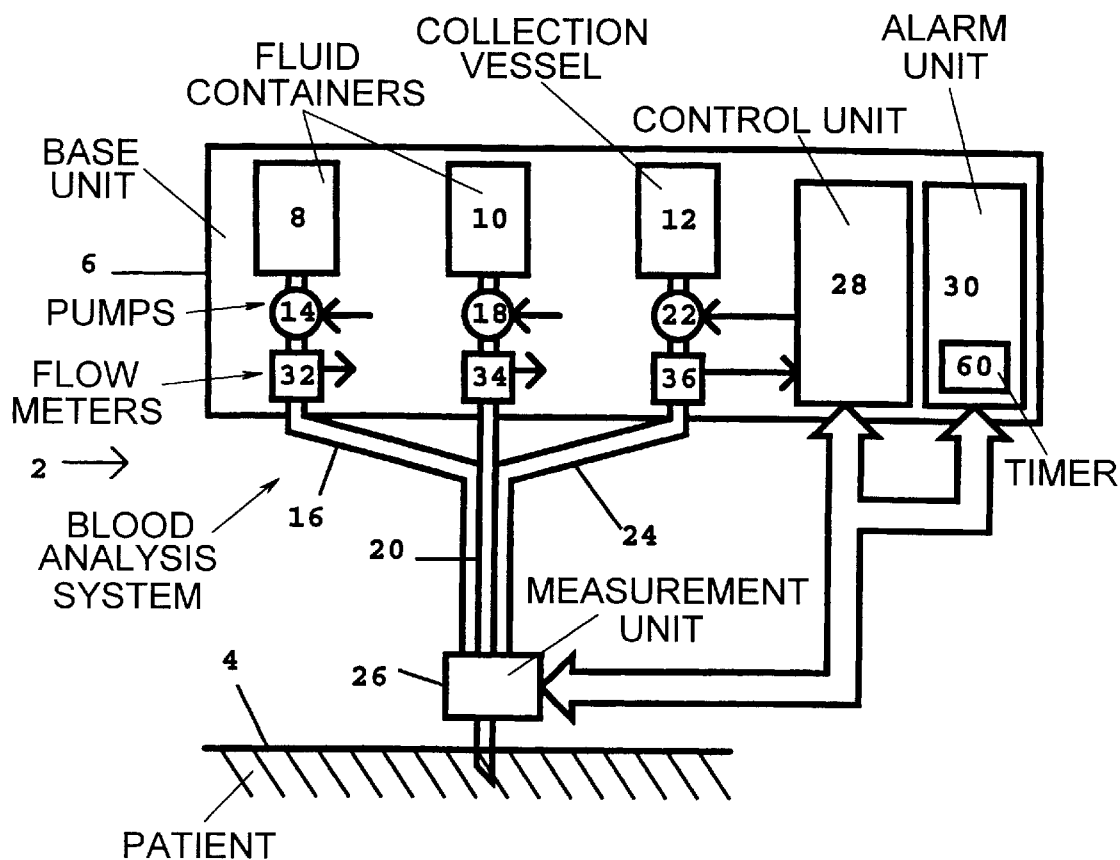
FIG. 1 shows one embodiment of the blood analysis system according to the invention.

FIG. 1 shows a blood analysis system 2 intended for measuring e.g. blood gases in a patient 4 to whom the blood analysis system 2 is connected. FIG. 1 schematically depicts the structure of the blood analysis system 2 in order to describe its function. The blood analysis system 2 includes a base unit 6 in which a first fluid container 8 and a second fluid container 10 are arranged. The fluid containers 8, 10 can hold flushing fluids, infusion fluids or calibration fluids. One and the same fluid can be employed for two or all of these purposes. The base unit 6 also contains a collection vessel 12 to hold spent fluids (waste fluids)

A first pump 14 is arranged at the first fluid container 8 to pump fluid from the first fluid container 8, a second pump 18 is arranged at the second fluid container 10 to pump fluid from the second fluid container 10 and a third pump 22 is arranged at the collection vessel 12 to pump fluid into the collection vessel 12. The pumps are controlled by a control unit 28.

Fluid from the first fluid container 8 is carried in a first tube 16 toward the measurement unit 26. Fluid in the second fluid container 10 is carried in a second tube 20 toward the measurement unit 26, and fluid to the collection vessel 12 is carried in a third tube 24. The three tubes 16, 20, 24, with the tube/catheter connection to the patient 4, for a tubing system. This tubing system is described in greater detail in conjunction with FIGS. 3 and 4 below.

The measurement unit 26 is arranged, near the patient 4, in the tubing system formed by tubes 16, 20, 24. This is to minimize any loss of blood and obtain fast readings with no risk of contamination of the blood sample. A short flow distance between the patient 4 and the measurement unit 26 also makes it easier to flush clean the parts of the tubes 16, 20, 24 in contact with blood. The measurement unit 26 is connected via a data bus to the control unit 28 and an alarm unit 30 in the base unit 6.

A first flow meter 32 for measuring the flow of the first fluid in the first tube 16, a second flow meter 34 for measuring the flow of the second fluid 34 in the second tube 20 and a third flow meter 36 for measuring the flow of fluid to the collection vessel 12 can also be arranged in the base unit 16. The flow meters 32, 34, 36 are connected to the control unit 28. Additional safety and monitoring of system operation can be achieved when the actual flow of fluids in the system is measured. For example, the volumes of fluid passing the respective flow meters 32, 34, 36 can be calculated.

Figure 2:
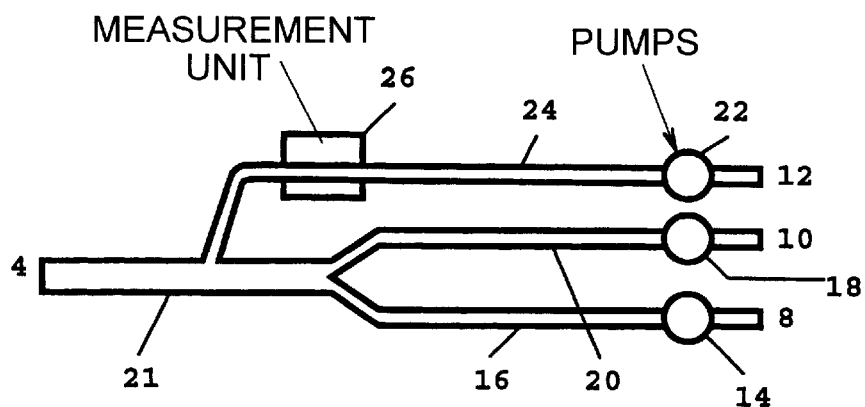
FIG. 2 shows a first location for a measurement unit in the tubing system of tubing in the blood analysis system of the invention.

FIG. 2 shows a first embodiment of the tubing system with the first tube 16 and the second tube 20 merged into a catheter 21 for connection to the patient 4, and the third tube 24 connected to the catheter between the first tube 16, the second tube 20 and the patient 4. Here, the measurement unit is located in the third tube 24.

The following flow control can be appropriate for this embodiment. The third pump 22 pumps fluid through the third tube 24 and accordingly draws blood from the patient into the third tube 24 and on into the measurement unit 26 for analysis. Blood in the common tube 21 (catheter) between the patient 4 and the branch to the third tube 24 is returned to the patient 4 when the first pump 14 or the second pump 18 is activated to flush the common tube 21 and the measurement unit 26.

Figure 3:
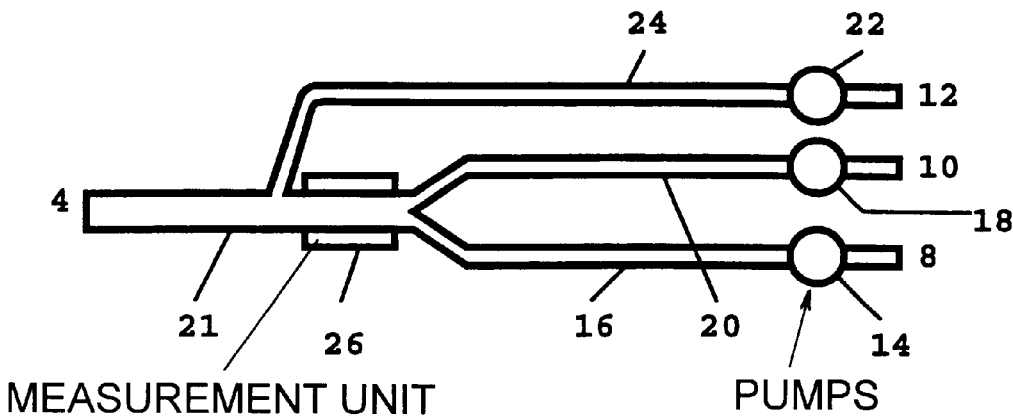
FIG. 3 shows a second location for the measurement unit in the tubing system in the blood analysis system of the invention.

FIG. 3 shows a second embodiment of the system of tubing, the only difference, in principle, being that the measurement unit 26 is located in the common tube 21 instead of in the third tube 24.

The method described above is not suitable for this embodiment, since the third pump 22 is unable to draw a blood sample to the measurement unit 26. An alternative method can be used instead. Either the first pump 14, or the second pump 18, can be used for drawing blood to the measurement unit 26. Since the tubes 16, 20 between the measurement unit 26 and the pumps 14, 18 are long (about 1–2 m) in relation to the distance between the measurement unit 26 and the patient 54 (about 1–20 cm), there is no risk of blood being suctioned through the entire tube 16, 20. All blood can then be returned to the patient 4 after analysis. Surplus flushing solution can be pumped into the collection vessel through the third tube 24.

Thus, the location of the measurement unit 26 primarily affects the way control of the blood analysis system is devised, mainly in respect to the pumps activated according to the measurement to be performed, i.e. measurement of one test sample or calibration of measurement sensors in the measurement unit 26. Although possible control procedures already have been described above, the basic principle of the method according to the invention is first described below in conjunction with descriptions of FIGS. 4–7.

Figure 4:
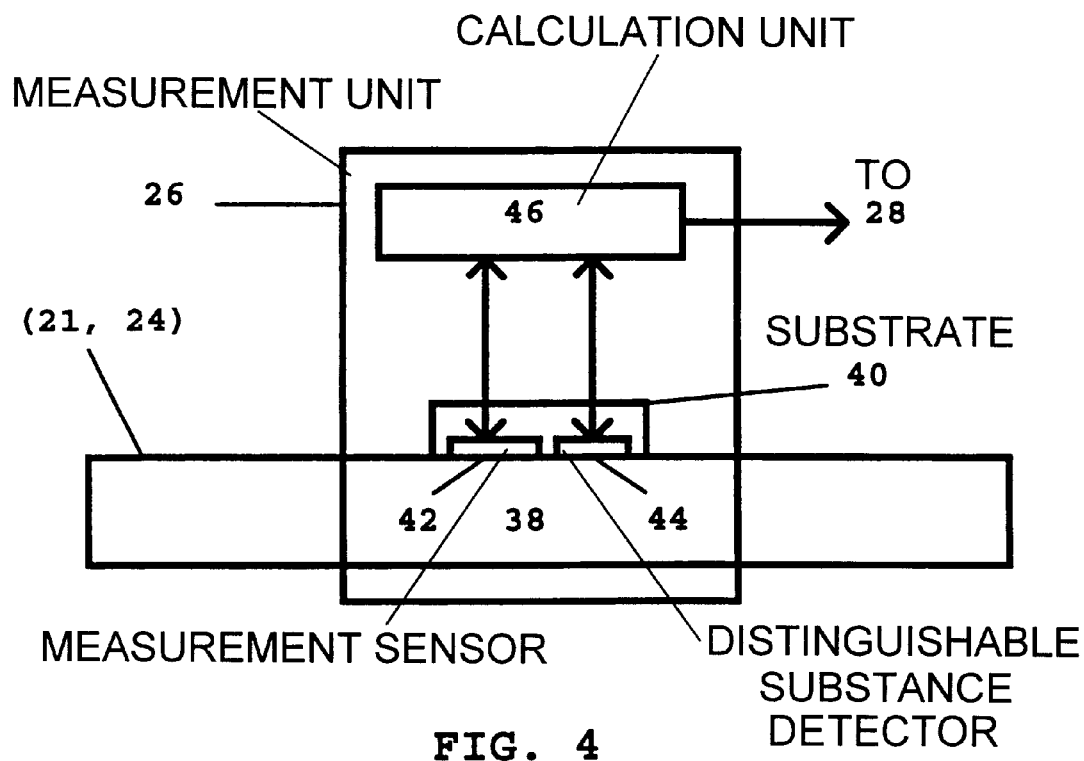
FIG. 4 shows one embodiment of the measurement unit in the blood analysis system of the invention.

One embodiment of the measurement unit 26 is shown in FIG. 4. As is evident from FIGS. 2 and 3, the measurement unit 26 can be arranged at the third tube 24 or the common tube 21. A measurement cell 38, through which the fluids can flow for measurement, is arranged in the measurement unit 26. A measurement sensor 42, preferably an electrochemical measurement sensor, and a detector 44 are arranged on a substrate 40, e.g. a chip, so they come into contact with fluid in the measurement cell 38. A calculation unit 46 which communicates with the control unit 28 in the blood analysis system is also arranged in the measurement unit 26. The fluid in the measurement cell 38, or a mixture of fluids in the measurement cell 38, can be identified by the detector 44. The method according to the invention is based on more accurate regulation and monitoring of the entire system by the control unit 28 according to identification of the fluid in the measurement cell 38. With the location of the measurement cell 26 shown in FIG. 2, control can be adapted according to the method so the third pump 22 is caused to pump a blood sample to the measurement unit 26. The detector 44 continuously senses the identity of the fluid in the measurement cell 38, the third pump 22 is stopped when the measurement unit 26 only contains blood and an analysis of the blood sample is performed. The first pump 14 is then activated and pumps fluid out of the first container. The third pump 22 is activated at the same time but with a reduced pumping effect so some of the fluid is conveyed to the patient 4 and some of the fluid is conveyed to the measurement unit 26. When the detector 44 senses that only the first fluid begin to fill the measurement cell 28, the pumping effect of the third pump 22 can be increased somewhat so fluid mainly flows through the measurement cell 38 in order to flush same. When the detector 44 only senses the presence of the first fluid in the measurement cell 38, the measurement sensor 42 can then be calibrated with the first fluid.

In two-point calibration, the second pump 18 and the third pump 22 are then activated so the second fluid is pumped from the second tube 20 to the common tube 21 and out into the third tube 4 and on to the measurement unit 26. In the same way as with the first fluid, the system waits until the detector only identifies the second fluid, whereupon the pumps 18, 22 are stopped, and the measurement sensor 42 is calibrated at a second measuring point. The third pump 22 can then be activated in order to draw a new blood sample from the patient 4. The detector 44 once again monitors the time at which the measurement cell 38 is filled with blood.

The system of tubing must be flushed between each blood measurement, however, performing two calibration measurements between each blood sampling is unnecessary. If the measurement cell 42 displays long-term stability, calibration with one fluid at certain intervals, e.g. every tenth measurement, may be sufficient. In this situation, the first fluid can be a pure flushing solution which flushes the entire system after each measurement, The second fluid can be a calibration fluid which is introduced into the measurement unit 26 through the second tube 20 only when calibration is to be performed.

The corresponding method principles also apply when the measurement unit 26 is located at the common tube 21 according to FIG. 3, however, the pumping sequence then differs somewhat.

When control is exercised with the method according to the invention, the blood analysis system is not as dependent on pump performance, pumping rate, pumping accuracy, the tubing and the effect of age, which occur when the system is used for an extended period of time. For the tubes in particular, manufacturing variations (differences between different manufacturers or differences in the quality of tubing materials) can result in differences in elasticity and tube lengths which could effect the operation of the blood analysis system if the system were not regulated in accordance with the method according to the present invention.

With the aid of an identification of the fluid in the measurement cell 38, a number of monitoring functions can be utilized for quickly sounding an alarm or stopping the blood analysis system if a fault should occur. Air bubbles entering the measurement cell 38 cause a major change in signals from the detector 44, and an alarm can be immediately triggered and the system stopped. This increases patient safety, and there is no risk of air bubbles entering the patient's blood circulatory system. This also means that it is easy to determine when a fluid is no linger available (because the container is empty or because a leak has developed somewhere in the system).

Even an occlusion of the tubing system can be detected. This is suitably performed by measuring time segments in the system. For example, a timer 60 in the alarm unit 30 in FIG. 1 measures the times required to pump fluid to and from the measurement unit 26, thereby utilizing detection of the identity of the fluid in the measurement cell 38 as a timing marker. As long as the times in each sampling cycle remain within reasonable limits (compared to predetermined values, compared to a preceding sampling cycle or compared to a mean value for a plurality of sampling cycles) the system is operating properly. If the deviation is too great, e.g. if a fluid does not reach the measurement unit 26 within a given period of time, the alarm unit 30 assumes that there is an occlusion in that part of the tubing system formed by tubes 16, 20, 24, and an alarm can be activated. In the corresponding manner, identification of a new fluid in the measurement unit 26 at a time when all the pumps are inactive is indicative of a leakage.

Identification of the liquid in the measurement cell 38 can 20 be performed in a number of ways. In accordance with the present invention, identification is guaranteed by ensuring that the fluids in the system, i.e. blood and flushing, infusion or calibration fluids, all have at least one unique distinguishing property which can be easily measured with the detector 44. A special substance with a desired property is added to one fluid. If necessary, all fluids could be tagged in a similar way with distinguishable substances. Since a fluid could be introduced unintentionally into the blood system of the patient, innocuous substances should used.

Figure 5:
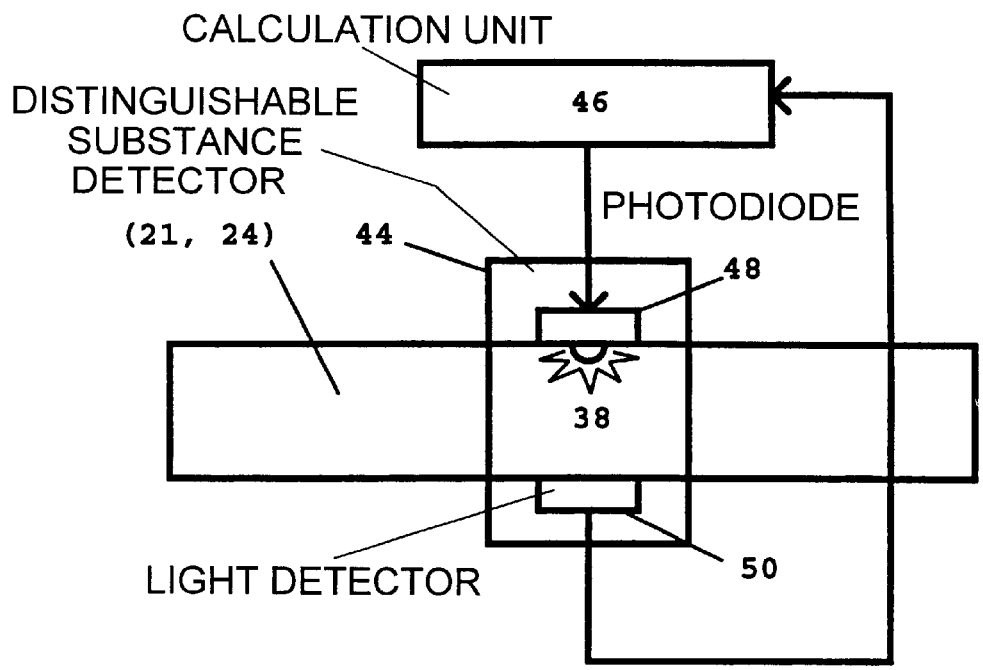
FIG. 5 shows a first embodiment of a detector in the measurement unit in the blood analysis system of the invention.

FIG. 5 shows a first embodiment of the detector 44. In this instance, the detector 44 is formed by a photodiode 48, which emits light under the control of the calculation unit 46, and a light detector 50 which senses light and supplies a corresponding electric signal to the calculation unit 46. With the optical device formed by the photodiode 48 and the light detector 50 e.g. the color of or the absorption in the fluid can be determined/detected. If color is to be determined, the fluids can be dyed to make then readily distinguishable from each other and from blood. If absorption is to be measured, substances giving the fluids distinctive absorption characteristics can be added to the fluids. When the property to be studied is selected in advance, the optical system can be devised in a relatively simple fashion. The photodiode 48 can have a number of light-emitting components which are alternately illuminated. The color of a fluid therefore can be easily determined if a respective photodiode is selected to match a specific fluid color. Filters alternately interposed in the light path can be used to produce absorption at distinct wavelengths. When the studied property is selectively chosen with the measurement method, even calculating the composition of mixtures of fluids, which occur when a new fluid (or blood) is to be pumped to/from the measurement unit 26, is easy.

Figure 6:
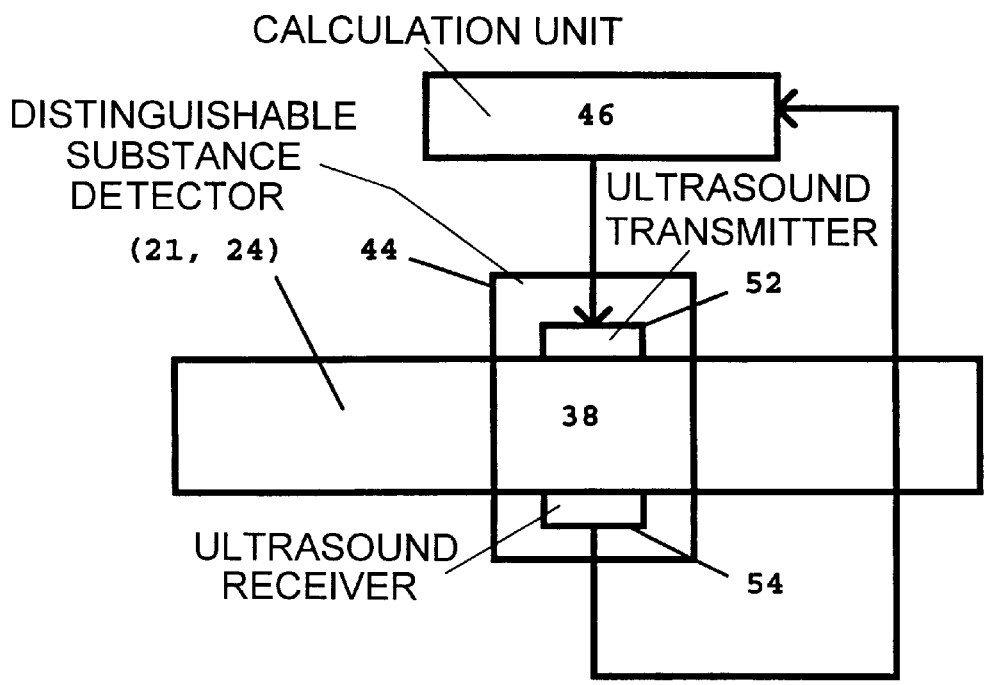
FIG. 6 shows a second embodiment of a detector in the measurement unit in the blood analysis system of the invention.

A second embodiment of the detector 44 is shown in FIG. 6. In this instance, the fluids have been tagged with acoustically distinguishable substances. The detector then also includes an acoustic measurement unit is formed by an ultrasound transmitter 52 and an ultrasound receiver 54, both connected to the calculation unit 46, for determining the identity of the fluid in the measurement cell 38. Here, the speed of sound, as well as acoustic damping or some other acoustic property, can be used for identifying the fluid.

Figure 7:
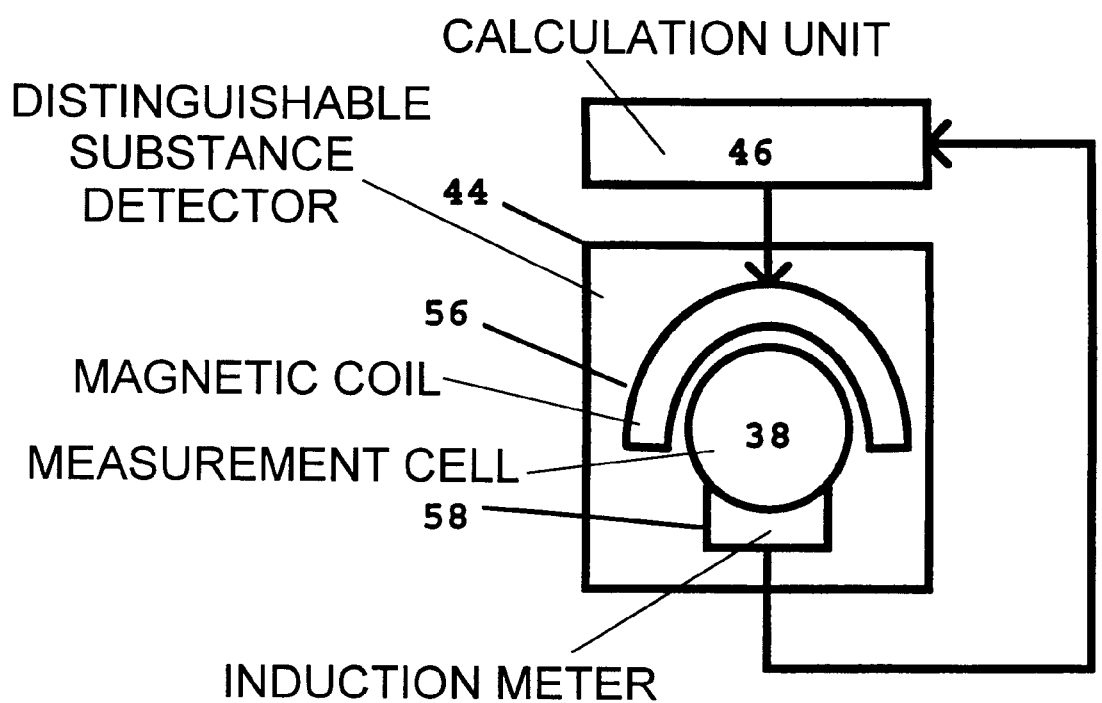
FIG. 7 shows a third embodiment of a detector in the measurement unit in the blood analysis system of the invention.

Finally, a third embodiment of the detector 44 is shown in FIG. 7. An electric and/or magnetic property has been utilized in this instance. Blood and calibration fluid in particular have both electric and magnetic properties making it possible for them to be measured with an electric and/or magnetic measurement device which is formed in this instance by a magnetic coil 56, which generates an alternating magnetic field, and an induction meter 58 which senses e.g. induced current (or an electromotive force) in the fluid in the measurement cell 38. Alternately, the fluid's capacitance, resistance or some other electric or magnetic property can be measured for identifying the fluid.

Although the embodiment of the blood analysis system shown in FIG. 1 has three containers, two of which are for fluids, and three pumps, the present invention will work equally well with other systems. As long as at least two fluids are used, identification of the fluids and blood can be made by using tag substances according to the invention in achieving more accurate control and more effective monitoring of the system.

The invention limited to the analysis of blood gases. The system and the method can be employed for all blood analyses which can be performed in a corresponding manner, however, the main advantages of the invention are achieved in on-line systems.

Although modifications and changes may be suggested by those skilled in the art, it is the intention of the inventor to embody within the patent warranted hereon all changes and modifications as reasonably and properly come within the scope of his contribution to the art.

I claim as my invention:

1. A blood analysis system comprising:
   a measurement unit;
   a measurement cell in said measurement unit;
   means for alternatingly filling said measurement cell with blood and one of at least two fluids, said at least two fluids including a calibration fluid for said measurement unit;
   at least one of said at least two fluids containing a distinguishable substance; and
   a detector disposed in said measurement unit in communication with said measurement cell for determining an identity of a fluid other than the calibration fluid in said measurement cell containing said distinguishable substance.

2. A blood analysis system as claimed in claim 1 wherein said distinguishable substance comprises a colorant and wherein each of said at least two fluids contains a colorant distinguishing each of said at least two fluids from each other and from blood, and wherein said detector comprises an optical detector for determining the identity of the fluid in the measurement cell.

3. A blood analysis system as claimed in claim 1 wherein said distinguishable substance comprises an optically active agent, and wherein said at least two fluids respectively contain different optically active agents making said at least two fluids distinguishable from each other and from blood, and wherein said detector comprises an optical detector for determining the identity of the fluid in the measurement cell.

4. A blood analysis system as claimed in claim 1 wherein said distinguishable substance comprises an acoustically active agent, and wherein said at least two fluids respectively contain different acoustically active agents making said at least two fluids distinguishable from each other and from blood, and wherein said detector comprises an acoustic detector for determining the identity of the fluid in the measurement cell.

5. A blood analysis system as claimed in claim 1 wherein said distinguishable substance comprises an electrically active agent, and wherein said at least two fluids respectively contain different electrically active agents making said at least two fluids distinguishable from each other and from blood, and wherein said detector comprises an electric detector for determining the identity of the fluid in the measurement cell.

6. A blood analysis system as claimed in claim 1 wherein said distinguishable substance comprises an magnetically active agent, and wherein said at least two fluids respectively contain different magnetically active agents making said at least two fluids distinguishable from each other and from blood, and wherein said detector comprises an magnetic detector for determining the identity of the fluid in the measurement cell.

7. A blood analysis system as claimed in claim 6 wherein said detector comprises means for identifying when said measurement cell is filled with blood or fluid, and wherein said control means comprises for pumping blood or fluid into said measurement cell until said output signal from said detector indicates that said measurement cell with blood or is filled with said one of said at least two fluids.

8. A blood analysis system as claimed in claim 1 wherein said means for alternatingly filling said measurement cell comprises a plurality of containers for the respective fluids and a plurality of tubes respectively connecting said plurality of containers to said measurement unit, and a plurality of pumps for pumping the respective fluids through the respective tubes, wherein said detector comprises means for generating an output signal identifying said identity of the fluid in the measurement cell, and said system further comprising control means, connected to said pumps and to said detector, for regulating said pumps dependent on said output signal from said detector.

9. A blood analysis system as claimed in claim 1 further comprising an electric chemical sensor disposed in said measurement unit on a substrate in said measurement cell, and wherein said detector comprises a detector integrated onto said substrate.

10. A blood analysis system as claimed in claim 9 further comprising a pump for pumping said one of said at least two fluids into said measurement cell, and wherein said control means comprises means for identifying whether the identity of fluid in the measurement cell has changed within a predetermined time after activation of said pump, as said condition indicative of proper operation of said blood analysis system.

11. A blood analysis system as claimed in claim 1 wherein said detector generates an output signal dependent on the identity of the fluid in the measurement cell, and said system further comprising control means, supplied with said output signal from said detector, for analyzing said output signal and identifying at least one condition indicative of proper operation of said blood analysis system, said control means generating a control means output signal in an absence of said at least one condition, and said system further comprising an alarm unit, supplied with said control means output signal, which generates an alarm upon receiving said control means output signal.

12. A blood analysis system as claimed in claim 11 wherein said control means comprises means for identifying whether said measurement cell contains at least some fluid or blood, as said condition indicative of proper operation of said blood analysis system.

13. A method for regulating a blood analysis system comprising the steps of:
    adding a distinguishable substance other than a calibrant to a first fluid and pumping said first fluid, with said distinguishable substance therein, into a measurement cell;
    determining an identity of the fluid in the measurement cell by monitoring said distinguishable substance in said first fluid in said measurement cell;
    terminating pumping of said first fluid into said measurement cell when said measurement cell is filled with said first fluid;

calibrating at least one measurement sensor in said measurement cell using said first fluid;

pumping blood into said measurement cell to replace said first fluid in said measurement cell;

identifying the presence of blood in said measurement cell;

terminating pumping of blood into said measurement cell when said measurement cell has filled with blood; and measuring at least one parameter of said blood with said measurement sensor in said measurement cell.

14. A method as claimed in claim 13 comprising the additional steps of:

adding a distinguishable substance to a second fluid and pumping said second fluid into said measurement cell;

determining an identity of fluid present in said measurement cell by monitoring said distinguishable substance in said second fluid;

terminating pumping of said second fluid into said measurement cell when said measurement cell is filled with said second fluid; and calibrating at least one measurement sensor in said measurement cell using said second fluid.

\* \* \* \* \*